United States Patent
Landscheidt et al.

[11] Patent Number: 5,649,322
[45] Date of Patent: Jul. 15, 1997

[54] PROCESS FOR THE PREPARATION OF $C_1$-$C_4$-ALKYL NITRITES

[75] Inventors: Heinz Landscheidt, Duisburg; Paul Wagner, Düsseldorf; Zoltan Kricsfalussy, Leverkusen; Alexander Klausener, Köln, all of Germany

[73] Assignee: Bayer Aktiengesellschaft, Leverkusen, Germany

[21] Appl. No.: 571,625

[22] Filed: Dec. 11, 1995

Related U.S. Application Data

[63] Continuation of Ser. No. 203,975, Mar. 1, 1994, abandoned.

[30] Foreign Application Priority Data

Mar. 8, 1993 [DE] Germany ............ 43 07 193.7

[51] Int. Cl.⁶ .................................................. C07C 203/02
[52] U.S. Cl. ........................................................... 558/488
[58] Field of Search ............................................. 558/488

[56] References Cited

U.S. PATENT DOCUMENTS

| | | | |
|---|---|---|---|
| 4,353,843 | 10/1982 | Doumaux, Jr. et al. | 558/488 |
| 4,908,466 | 3/1990 | Nelson | 558/488 |

FOREIGN PATENT DOCUMENTS

| | | |
|---|---|---|
| 0046983 | 3/1982 | European Pat. Off. . |
| 0076217 | 4/1983 | European Pat. Off. . |
| 0310191 | 4/1989 | European Pat. Off. . |
| 0425197 | 5/1991 | European Pat. Off. . |

*Primary Examiner*—Sharon Gibson
*Assistant Examiner*—Valerie Fee
*Attorney, Agent, or Firm*—Sprung Horn Kramer & Woods

[57] ABSTRACT

$C_1$-$C_4$-Alkyl nitrites can be prepared by reaction of $C_1$-$C_4$-alkanols with nitrogen oxides with the participation of oxygen in a reactor designed as a scrubber column, nitrogen oxides having a proportion of more than 50% of NO of the total amount of gram atoms of N of the nitrogen oxides, oxygen and optionally inert gas being fed into the lower part of the reactor. 5 to 60% of the total amount of $C_1$-$C_4$-alkanol used is likewise fed into the lower part of the reactor in vaporous or atomized form, while the remaining $C_1$-$C_4$-alkanol is delivered to the column head.

19 Claims, 1 Drawing Sheet

PROCESS FOR THE PREPARATION OF $C_1$-$C_4$-ALKYL NITRITES

This application is a continuation of application Ser. No. 08/203,975, filed Mar. 1, 1994 now abandoned.

BACKGROUND OF THE INVENTION

1. Field of the Invention

The present invention relates to an industrial process for the preparation of alkyl nitrites from nitrogen oxides, oxygen and lower alkanols, the nitrogen oxides having a proportion of more than 50% of NO of the total amount of gram atoms of N of the nitrogen oxides being used. Some of the lower alkanol is used in the lower part of the reactor together with the nitrogen oxides and the remaining part is charged in the upper part of the reactor.

Alkyl nitrites (alkyl esters of nitrous acid) have a varied use, for example as additives for motor oils, as stabilizers for unsaturated organic compounds, as spasmolytics, as reagents for oximations, nitrosations and diazotizations and as intermediates for chemical syntheses.

2. Description of the Related Art

It has long been known that alkyl nitrites, including in particular methyl nitrite, can be prepared by reaction of nitrogen oxides with the corresponding alkanols, including in particular methanol, with the participation of an amount of oxygen adapted to the amount and composition of the nitrogen oxides used. For example, in the preparation of methyl nitrite from nitrogen oxides, oxygen and methanol, fundamentally the following reactions shown can proceed between the participating components:

$$2\ NO + O_2 \rightarrow 2\ NO_2 \tag{1}$$

$$NO_2 + NO \rightleftharpoons N_2O_3 \tag{2}$$

$$R\text{—}OH + N_2O_3 \rightarrow R\text{—}ONO + HNO_2 \quad (R=CH_3) \tag{3}$$

$$R\text{—}OH + HNO_2 \rightarrow R\text{—}ONO + H_2O \tag{4}$$

$$N_2O_3 + H_2O \rightarrow 2\ HNO_2 \tag{5}$$

$$2\ NO_2 \rightleftharpoons N_2O_4 \tag{6}$$

$$R\text{—}OH + N_2O_4 \rightarrow R\text{—}ONO + HNO_3 \tag{7}$$

$$N_2O_4 + H_2O \rightarrow HNO_2 + HNO_3 \tag{8}$$

In the preparation of the target alkyl nitrites, the procedure is preferably followed so that as far as possible only the reactions reproduced in reaction equations (1) to (4) proceed and water is obtained as the sole waste material. The reaction reproduced in reaction equation (5) is generally unavoidable since the added dinitrogen trioxide, and that formed according to reaction equation (2) can react to completion not only with the alcohol in accordance with reaction equation (3), but also with the water resulting according to reaction equation (4). However, in the presence of sufficient, in particular excess, amounts of alcohol, the nitrous acid resulting in this case in accordance with reaction equation (4), is scavenged with formation of the desired alkyl nitrite and water, that is is not lost for example as waste material.

The reactions reproduced in the reaction equations (6) to (8) are undesirable since they lead to the irreversible formation of nitric acid. Formation of this by-product reduces the yield of desired alkyl nitrite, based on nitrogen oxide used. The resulting nitric acid must be separated off and, in particular, on carrying out the overall process on an industrial scale, waste waters are produced in this case which must receive secondary treatment with not insignificant expenditure. In order to exclude as far as possible the dimerization proceeding according to reaction equation (6) of the nitrogen dioxide either added in a mixture with nitrogen monoxide or formed via equation (1), which dimerization initiates the formation of nitric acid, the stoichiometric ratio of nitrogen monoxide to nitrogen dioxide is preferably adjusted so that it adopts a value >1. In this manner the formation of dinitrogen tetroxide is successfully repressed in favour of dinitrogen trioxide.

As can be seen from the reaction equations (1) to (3), during the feed-in of nitrogen oxides to prepare alkyl nitrites, the following procedure can be advantageously followed for example:

Nitrogen monoxide and nitrogen dioxide are fed in separately or as a mixture, a molar ratio $NO:NO_2$ of >1 occurring, which according to the above statements likewise reduces the probability of formation of dinitrogen tetroxide and, in association with this, has as a consequence the repression of the formation of nitric acid.

Oxygen is additionally fed in, separately from the nitrogen oxides or as a mixture with them, more precisely preferably in a molar ratio $NO:O_2$ of >4, based on the number of moles of NO, which exceeds the number of moles of $NO_2$ used, which in correspondence with the above statements has the consequence of preference of the formation of dinitrogen trioxide in comparison to that of dinitrogen tetroxide and, associated with this, a repression of the formation of nitric acid.

A series of industrially interesting continuous processes is known in which the formation of, for example, methyl nitrite in the gas phase proceeds within an overall process, which is characterized in that, in it, methyl nitrite functions as an oxidizing agent, cocatalyst, alkoxylation reagent or other type of reaction partner. It is typical for this process that in its course, the nitrogen monoxide formally contained in the methyl nitrite is not consumed, but is liberated as a gas. In a preferred embodiment of reactions of this type, the freshly generated methyl nitrite is introduced together with the additional reaction partner or reaction partners and reaction auxiliaries into the reaction space or the reaction vessel and the portion of the product gas stream remaining in the gaseous state which contains the nitrogen monoxide formed in the course of the reaction is returned to the reactor for the methyl nitrite preparation after separating off as far as possible the condensed or condensable reaction product or reaction products. This closes a cyclic process, based on nitrogen monoxide and methyl nitrite. The principle of such a process is depicted in FIG. 1.

Reactions in which such a continuous cyclic procedure is particularly advantageous are for example the following:

(A) The preparation of dimethyl oxalate from carbon monoxide in the presence of suitable catalysts [cf. EP 46 598]

$$2CO + 2CH_3ONO \xrightarrow{[CAT]} H_3COOC\text{—}COOCH_3 + 2NO$$

(B) The oxidation of unsubstituted or substituted olefins in the presence of methanol and suitable catalysts

[cf. EP 55 108]

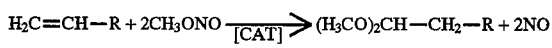

(C) The preparation of dimethyl carbonate from carbon monoxide in the presence of suitable catalysts [cf. EP 425 197 and Zeitschrift f. Katalyt. Forschung, (China), Vol. 10(1), p. 75–78 (1989)]

The reactions mentioned are carried out in the gas phase or alternatively in the liquid phase. In the latter case, methanol is preferably used as solvent. It is generally characteristic that both the methyl nitrite fed and also the nitrogen monoxide formed are supplied and conducted away, respectively in the gaseous state. The gas circulated can, depending on the selected reaction conditions, the concentration and the physicochemical characteristics of the participating components as well as the phase equilibrium contain still further substances beyond methyl nitrite and/or nitrogen monoxide. Inert gases, such as carbon dioxide, nitrogen and argon, reactants such as carbon monoxide and olefins (cf. (B), for example methyl acrylate), reaction products, such as dimethyl oxalate (cf. (A)) and dimethyl carbonate (cf. (C)) as well as methanol dissolved in the gas stream can be mentioned here by way of example.

Dimethyl oxalate is of great interest as an intermediate, for example for the preparation of ethylene glycol, which itself has broad use as solvent, coolant and as raw material for the fabrication of polyester fibres and alkyd resins.

Acetals, as described under (B), are important starting materials for the preparation of heterocycles, which are themselves used as intermediates in the synthesis of pharmaceutical and agrochemical active compounds.

Dimethyl carbonate is used as a less toxic methylation reagent, in comparison to, for example methyl chloride or dimethyl sulphate, as a propellant additive and as starting material for the preparation of diphenyl carbonate. Diphenyl carbonate serves as an intermediate for the preparation of isocyanates and polycarbonates.

Taking the requirements below into account is essential for the successful operation of continuous processes as mentioned in the examples (A), (B) and (C):

The oxygen fed in for regenerating the methyl nitrite from the returned nitrogen monoxide is to be reacted as completely as possible to form methyl nitrite.

This applies equally to all higher nitrogen oxides situated within the methyl nitrite generator, namely to nitrogen dioxide, dinitrogen trioxide and dinitrogen tetroxide.

The reaction conditions and the reaction technique are to be optimized so that the undesirable formation of the by-product nitric acid (cf. reaction equations (7) and (8)) is excluded as far as possible. This simultaneously serves for a maximum possible yield of desired alkyl nitrite.

The complete reaction of the fed oxygen or of the higher nitrogen oxides to give the desired alkyl nitrite is to take place within the alkyl nitrite generator. This avoids, in the case of an incomplete reaction of the participating components within the reaction space provided, complete reaction only occurring downstream of the alkyl nitrite generator and the reaction water (cf. reaction equation (4)) formed in this case being carried over into any downstream reaction which can possibly lead to undesirable side reactions there.

The reaction water resulting in the course of formation of the desired alkyl nitrite and the nitric acid (cf. reaction equations (7) and (8)), possibly formed as a consequence of undesirable side reactions, are to be separated off as completely as possible from the gaseous product stream which leaves the alkyl nitrite generator.

The heat of reaction released in the course of the reaction proceeding within the alkyl nitrite generator is to be conducted away.

In view of the safety requirements of the industrial execution of processes in which the alkyl nitrite generators of the principal mentioned here are integrated, local overheating and the formation of ignitable mixtures must be avoided.

All the requirements mentioned are satisfied by the process according to the invention in a simple manner surpassing the prior art.

In Patent Application EP 310 191, which describes quite generally a process for the preparation of alkyl nitrites, in particular methyl nitrite and ethyl nitrite, with participation of oxygen in the reaction, it is proposed to configure the entire reaction vessel, in which the reaction between oxygen, nitrogen monoxide and the particular alcohol takes place, as a scrubber having two spatially separated zones, a reaction zone and a rectification zone. The scrubbing medium, preferably identical to the alcohol brought to the reaction and used as such in stoichiometric excess, is fed in by the counter-current principle at the head of the rectification zone and conducted away in opposite direction to the rising product gas stream composed inter alia of the alkyl nitrite and the water produced during its formation. A disadvantage in this case is the separate layout of reaction zone and rectification zone which requires a high expenditure in terms of apparatus.

According to the patent application mentioned, the rectification zone is laid out in the form of a tray column. A disadvantage of such a procedure is that a completely mixed gas zone is present above each tray, back mixing effects occurring. In order, despite this, to realize the desired separation effect, that is the removal of the water produced in the course of formation of the alkyl nitrite and the water-soluble by-products, such as for example nitric acid, the entire apparatus must be dimensioned significantly larger than would be possible with the exclusion of back-mixing effects. It can be noted that, for example, any nitric acid contained in the product gas stream leaving the alkyl nitrite generator, or even water, can interfere even in the smallest amounts highly sensitively with the downstream process, for example the preparation of dimethyl oxalate or dimethyl carbonate.

In the same patent application it is described that the heat of reaction released in the production of the alkyl nitrite can be removed by withdrawing from the reaction zone a liquid side stream which, after external cooling, is fed back into a higher-situated part of the reaction zone. However, apart from an increased expenditure in terms of apparatus, this has the additional disadvantage that the concentration and the residence time of the reaction water formed within the reaction zone are thereby increased and prolonged, respectively. In this case, on the one hand an increased formation of by-products can occur, on the other hand, the use of increased amounts of scrubbing liquid, especially of methanol in the case of the methyl nitrite preparation, and possibly a further enlargement of the rectification zone are required in order to keep the product gas mixture exiting at the head of the overall reactor as far as possible water-free.

Finally, all data which are to be inferred from the Patent Application EP 310 191 mentioned are based only on computer simulation calculations. The only example, likewise based on such a computer simulation is not reproducible for those skilled in the art, since firstly, the mass flow rates entering and exiting, based on the alkyl nitrite reactor, are not specified and, secondly, no data are given on the reaction volumes, which alone decide on the residence time required by the reaction kinetics given. The actual efficiency of the arrangement of apparatus described is therefore insufficiently documented and can thus not be evaluated at all. Furthermore, the example mentioned is also irrelevant from industrial aspects, since it apparently contains no rendering inert of the fundamentally ignitable alkyl nitrite stream and therefore the carry-over effect due to the inert gas portion occurring when a procedure of sufficient safety is used is not taken into account. Since, for example, the lower explosion limit of the system alkyl nitrite/nitrogen monoxide/carbon monoxide/alcohol/inert gas is shifted towards lower alkyl nitrite concentrations with increasing pressure, this question is of highly decisive importance in cyclic processes, such as for example the industrial preparation of dimethyl oxalate or dimethyl carbonate, in which such gas mixtures are fed into alkyl nitrite reactors.

The object was therefore still to find a process for the continuous preparation of $C_1$–$C_4$-alkyl nitrites from the underlying $C_1$–$C_4$-alkanols, oxygen and nitrogen oxides, which takes into account the abovementioned requirements and is suitable for integration into continuous processes in which $C_1$–$C_4$-alkyl nitrites are consumed with release of NO.

SUMMARY OF THE INVENTION

The invention relates to a process for the preparation of $C_1$–$C_4$-alkyl nitrites by reaction of $C_1$–$C_4$-alkanols with nitrogen oxides and oxygen, characterized in that the reaction is carried out in a reactor designed as a scrubber column, oxygen and nitrogen oxides being fed into the lower part of the reactor, the nitrogen oxides representing a mixture of one or more selected from the group comprising NO, $N_2O_3$, $NO_2$ and $N_2O_4$, of which NO is always present and that is in an amount of more than 50% of the total amount of gram atoms of N of the nitrogen oxides, the nitrogen oxides being mixed with one or more inert gases, the proportion of which is 0–90% by volume of all gases used, the amount of oxygen being 0.15–0.3 mol per mole of the number of moles of NO which exceeds the number of moles of $NO_2$, the amount of alkanol being 0.8–2 mol per gram atom of N of the nitrogen oxides, the alkanol being injected at 5–60% of its total amount in vaporous or atomized form likewise into the lower part of the reactor and the remaining alkanol being fed into the upper part of the reactor, 10°–150° C. and 0.5 to 6 bar being employed and a residence time of the reaction partners in the reactor being set to 1–500 sec.

Figure 1:
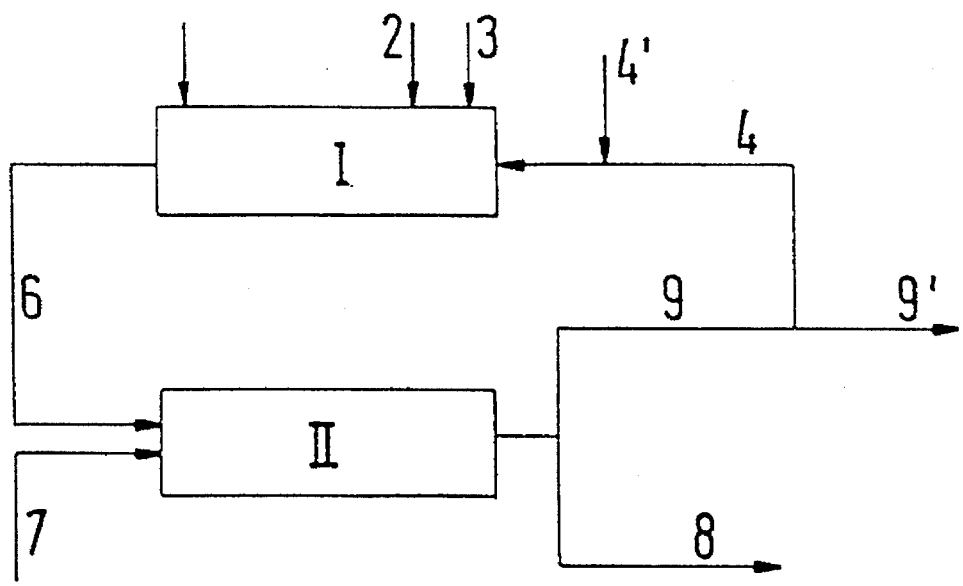
FIG. 1 shows a prior art reactor I for the formation of the alkyl nitrite (for example the methyl nitrite) and a reactor II for carrying out the described reactions (A), (B) or (C) or a still further reaction retiring alkyl nitrite. Alkyl nitrite formed in I flows via line (6) to II, where it is reacted with further starting materials fed via (7). The substances running out of II are separated into the desired products (8) and by-products (9), which chiefly contain the NO mentioned. The NO-containing by-products are conducted via (4) to I. A part of the by-products can be ejected via (9') as a purge stream in order to stop by-products other than NO increasing above a predetermined level. The losses of NO arising via (9') and losses occurring in other ways can be made up via (4').

To atomize the alkanol at (2), inert gas of the above described type can be used. In the preferred above-described variant of combining the feed streams (2), (3) and (4), the gas stream of the nitrogen oxide and the inert gas as well as oxygen can be used for vaporizing the alkanol.

DETAILED DESCRIPTION OF THE INVENTION $C_1$–$C_4$-alkanols for the process according to the invention are for example methanol, ethanol, propanol, isopropanol, butanol, sec-butanol, i-butanol, preferably methanol and ethanol, particularly preferably methanol. Accordingly, the $C_1$–$C_4$-alkyl nitrites derived therefrom are prepared, preferably methyl nitrite and ethyl nitrite, particularly preferably methyl nitrite.

In the process according to the invention oxygen participates in the reaction.

According to the invention, the aim is to form, as a reaction partner of the $C_1$–$C_4$-alkanol, dinitrogen trioxide, as corresponds to the above equations (3), (4) and (5).

An important reaction proceeding according to the invention is therefore the formation of $N_2O_3$, from NO and $NO_2$ (equation (2)), for which $NO_2$ is formed from NO and $O_2$ (equation 1)).

Furthermore, $N_2O_3$ can be used as such or as a mixture with nitrogen monoxide. Finally, mixtures nitrogen monoxide/nitrogen dioxide or nitrogen monoxide/nitrogen tetroxide mixtures, which can each react to form dinitrogen trioxide, can be used. The mixture of the nitrogen oxides to be used can also contain all species mentioned, that is NO, $N_2O_3$, $NO_2$ and $N_2O_4$. However, in each case, NO is present in an amount of more than 50% of the total amount of gram atoms of N of the nitrogen oxides, preferably an amount of 51–100%, particularly preferably 70–100%, highly particularly preferably 80–100%.

For the desired provision of $N_2O_3$ from NO, oxygen is used in a molar amount of 0.15–3 mol, preferably 0.2–0.27 mol, particularly preferably 0.23 to 0.25 mol per mole of the number of moles of NO which exceeds the number of moles of $NO_2$. Any $N_2O_4$ present is counted in this case as 2 mol of $NO_2$. It must be taken into account in this case that NO is already converted by reaction with any $NO_2$ or $N_2O_4$ present to give $N_2O_3$.

The NO amount, on which the oxygen used is based in the molar ratios given is therefore always that which exceeds in gram atoms of N the gram atoms of N in the $NO_2$ and $N_2O_4$.

The nitrogen oxides or nitrogen oxide mixtures to be used according to the invention can be used in principal without mixing with inert gases. However, an inert gas or a mixture of a plurality thereof is preferably added. The proportion of the inert gas or of the inert gases is accordingly 0–90% by volume of all gases used, preferably 10 to 80% by volume, particularly preferably 20 to 70% by volume. The inert gases which are useful in this case are all those which do not chemically react with the starting materials or the reaction products. Preferably, these are in this case one or more of the gases selected from the group comprising $CO_2$, $N_2$, Ar, He, preferably from the group comprising $CO_2$ and $N_2$.

It is an essential feature of the process according to the invention that the $C_1$–$C_4$-alkanol to be reacted is used at two positions in the reactor. 5 to 60% of the total amount used thereof, preferably 10 to 50%, particularly preferably 10 to 30% of the $C_1$–$C_4$-alkanol is used in the lower part of the reactor in vaporized or atomized form, while the remaining $C_1$–$C_4$-alkanol is delivered to the reactor head. Preferably, the portion of $C_1$–$C_4$-alkanol used in the lower part of the reactor is used in atomized form; the mean droplet diameter in this case is 5 to 1,000 µm, preferably 5 to 500 µm.

A preferred variant is, furthermore, to use the three starting material streams, which are used according to the invention in the lower part of the reactor, that is the $C_1$–$C_4$-alkanol, the oxygen and the nitrogen oxide stream, optionally in a mixture with inert gases, as a combined mass stream. In such a case, in combination with the preferred atomization of the $C_1$–$C_4$-alkanol portion, the stream of the feed gases (nitrogen oxide, optionally with inert gas and oxygen) can be used for atomizing the alkanol portion.

The total amount of $C_1$–$C_4$-alkanol used, that is both the part used in the lower part of the reactor and the part used in the upper part of the reactor, is together 0.8 to 2 mol per gram atom of nitrogen in the dinitrogen trioxide (or its precursor mixtures), preferably 1 to 1.5 mol, particularly preferably 1 to 1.2 mol. The overall range therefore includes a slightly substoichiometric proportion, within which the undesirable side-reactions are tolerated up to a certain extent, up to a superstoichiometric proportion but preferably a virtually equimolar proportion or slightly above.

The process according to the invention is carried out at a temperature of 10° to 150° C., preferably at 30° to 100° C., and at a pressure of 0.5 to 6 bar, preferably 0.8 to 5 bar, particularly preferably 1 to 4 bar, a residence time of the reaction partners in the reactor being set at 1 to 500 sec., preferably 5 to 300 sec., particularly preferably 10 to 50 sec. Temperature, pressure and residence time can fundamentally be adjusted independently of each other.

The reactor for the process according to the invention is a reactor designed as a scrubber column. Such columns are furnished with internals which are known in principal and which ensure an intimate liquid/gas mixing. Such internals are essentially the same as those which are conventional in the performance of thermal separation operations, for examples trays having bubble caps, sieve trays, valve trays, slotted trays and others known to those skilled in the art; in addition, packings of all types, having arranged packings, preferably structured packings, can be used; in addition, other internals such as baffle plates and chicane plates are useful.

Figure 2:
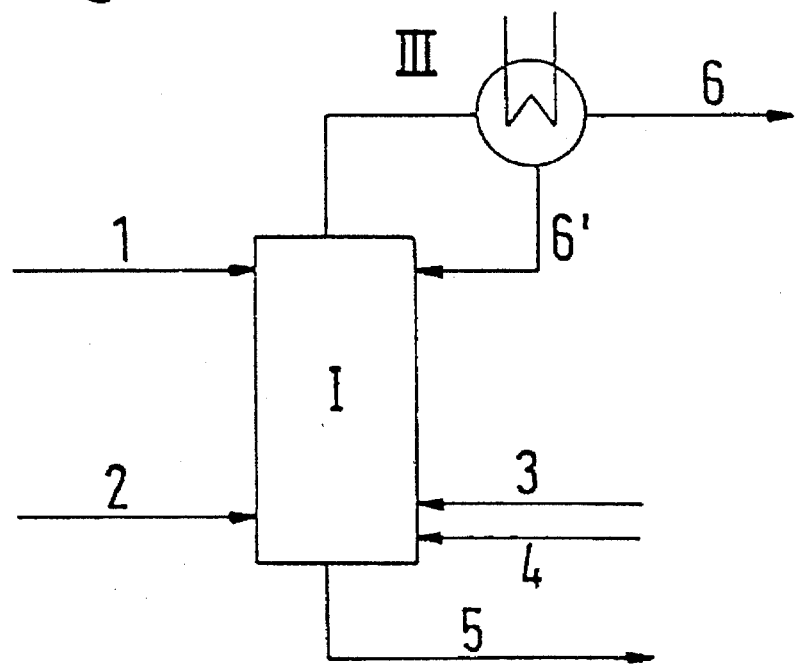
FIG. 2 shows a reactor I, designed as a scrubber column, having a cooler III mounted at the head of I. The alkanol to be reacted is supplied at the two positions (1) in the upper part and (2) in the lower part of the reactor. The alkanol stream at (2) is supplied in vaporized or atomized form. At (3), oxygen is supplied. At (4), nitrogen oxides are supplied in the manner described above, optionally mixed with inert gas. The product gas stream is taken off at the head of the reactor and passed through the cooler III. In this cooler, condensable portions of the product stream, for example entrained alkanol, are condensed and returned via (6') to the head of the column, preferably above the alkanol feed (1). The remainder is taken off via (6). Reaction water (5) is taken off at the bottom of the column. This reaction water contains co-produced nitric acid and alkanol supplied in excess.

The process according to the invention can be described by way of example with the aid of the accompanying FIG. 2:

In a preferred embodiment, the process according to the invention is a component of a continuous overall process within which $C_1$–$C_4$-alkyl nitrite functions as oxidizing agent, as cocatalyst, as alkoxylation reagent or as another type of reaction partner, but where the nitrogen monoxide formally contained in the alkyl nitrite is not consumed for the preparation of the product but is released again in gaseous form, remains in the product gas stream after separating off the condensed or condensable reaction products and is available for return into the alkyl nitrite synthesis. A closed cyclic process (cf. FIG. 1), with reference to nitrogen monoxide, is thus present. Apart from the nitrogen monoxide (0 to 50% by weight, preferably 5 to 40% by weight) mentioned, the return stream further contains inert gas, such as for example nitrogen, carbon dioxide, argon or helium (20 to 80% by weight, preferably 30 to 70% by weight), possibly unreacted alkyl nitrite (0 to 30% by weight, preferably 0 to 20% by weight) and/or other components such as for example incompletely reacted carbon monoxide (0 to 20% by weight), alkanol, reaction products incompletely condensed out and/or other gaseous substances. Possible losses of nitrogen oxide, which can occur in principle in the course of the methyl nitrite preparation, the downstream synthesis of the reaction product, its isolation, the return of the cyclic gas stream or the removal from the cycle of a part-stream of the cyclic gas stream (purge stream), can be compensated for by feeding in fresh nitrogen oxide. Nitrogen monoxide, nitrogen dioxide, dinitrogen trioxide and dinitrogen tetroxide can be used for this. The amount of the nitrogen oxide additionally to be fed in if required is 0 to 50% by weight, preferably 0 to 25% by weight, particularly preferably 0 to 10% by weight of the nitrogen oxide already situated in the returned cycle gas. The feeding in of this supplementarily fed nitrogen oxide can be carried out into the cycle gas stream, for example directly upstream of the introduction into the alkyl nitrite reactor. Together with the freshly supplied oxygen and the alkanol, this results in the reaction mixture for the desired alkyl nitrite formation by the process according to the invention. Within the continuous overall process, the process requiring a $C_1$–$C_4$-alkyl nitrite is preferably one of the processes of dialkyl carbonate preparation described further above as (A), (B) or (C), particularly preferably that described as (C).

The process according to the invention has various advantages:

The reaction conditions and the reaction technique can be optimized so that the undesirable formation of the by-product nitric acid is excluded as far as possible. As a result, at the same time, a maximum yield of the desired alkyl nitrite is achieved. Surprisingly, it proves to be particularly advantageous for the target minimization of the undesirable formation of nitric acid if the reactant gas fed in, namely the nitrogen monoxide and the oxygen, if at all possible directly after their combination and on entry into the reactor, are already brought into contact with a suitable amount of alkanol with as rapid and complete as possible mixing of all components. Precisely this is effected by the preferred use of a nozzle for this operation in the combination according to the invention with the feeding in of part of the methanol into the lower region of the reactor.

The complete conversion of the oxygen and of the higher nitrogen oxides fed in to give the desired alkyl nitrite proceeds within the alkyl nitrite generator. This avoids, in the case of an incomplete reaction of the participating components within the reaction space provided, a complete conversion only arising downstream of the alkyl nitrite generator and the reaction water produced in this case being carried over into any downstream reaction in which the alkyl nitrite prepared is further reacted, as a result of which undesirable side reactions can possibly be caused. If it is nevertheless desired to achieve an incomplete conversion of nitrogen oxides and, for example, to obtain a product gas mixture in which still unreacted nitrogen monoxide is present, this can equally be realized by the process according to the invention, for example by overdosing the nitrogen monoxide fed.

The reaction water produced in the course of the formation of the desired alkyl nitrite and the nitric acid possibly formed as a consequence of undesirable side reactions are virtually completely separated off from the gaseous product stream which leaves the alkyl nitrite generator.

The heat of reaction liberated in the course of the reactions proceeding within the alkyl nitrite generator is completely conducted away. Surprisingly, this proceeds particularly smoothly, if in the feeding in according to the invention of a part of the alkanol into the lower region of the reaction vessel, proceeding jointly with the feed of the gaseous reactants, namely nitrogen monoxide and oxygen, this methanol is introduced in liquid form (atomized instead of vaporized).

With regard to the safety requirements of the industrial implementation of processes into which are integrated alkyl nitrite generators of the principle mentioned here, local overheating and the production of ignitable mixtures are avoided.

The process according to the invention is suitable in particular for the integration into continuous processes in which the formation of the alkyl nitrite in the gas phase proceeds within an overall process which is characterized in that alkyl nitrite functions therein as oxidizing agent, as cocatalyst, as alkoxylation reagent or as another type of reaction partner, in which the nitrogen monoxide formally contained in the alkyl nitrite is not consumed for the preparation of the product but is released as gas and in which the product gas stream remaining after separating off the condensed or condensable reaction products, and the nitrogen monoxide contained therein, are available for return to the alkyl nitrite synthesis, thus representing therefore a closed cyclic process (cf. FIG. 1) with reference to nitrogen monoxide and alkyl nitrite.

EXAMPLES

Example 1

Preparation of Methyl Nitrite from Nitrogen Monoxide, Oxygen and Methanol

A reactor system was used as schematically depicted in FIG. 2 (volume of the reactor I 16.0 l, 9 theoretical separation stages, head pressure 3,030 mbar, equipped with a heat exchanger III mounted at the head of the reactor). In the table the fed and discharged streams are indicated by the numbers taken from FIG. 2. Stream (1) and (5) are liquid (fl.), stream (2), depending on the process variant selected, is liquid (fl.) or gaseous (g.), and streams (3), (4) and (6) are gaseous (g.). While streams (1), (2), (3) and (4) specify and quantify the reactants used, the experimentally resulting contents of the listed components in the product gas stream are reproduced as stream (6) and in the outlet as stream (5).

Within the limits of the imprecision of measurement, the streams contained the following substances:

| Stream (1) (fl.) | | Stream (2) | | Stream (3) (g.) | |
|---|---|---|---|---|---|
| MeOH | 2010 g/h | MeOH (g.) | | 502 g/h O$_2$ | 520 g/h |
| Stream 4 (g.) | | Stream 5 (fl.) | | Stream 6 (g.) | |
| NO | 1922 g/h | MeOH | | 74 g/h CO$_2$ | 3373 g/h |
| CO$_2$ | 3373 g/h | HNO$_3$ | | 40 g/h NO | 14 g/h |
| | | Water | | 560 g/h MeOH | 422 g/h |
| | | | | MeONO | 3840 g/h |
| | | | | Water | <1.5 g/h |
| | | | | HNO$_3$ | 0 g/h |

MeOH=CH3OH; MeONO=CH3ONO

The product gas mixture (stream (6)) had a temperature of 35° C. on leaving the heat exchanger III.

Example 2

Preparation of Methyl Nitrite from Nitrogen Monoxide, Nitrogen Dioxide, Oxygen and Methanol Performance of the trial and designation of the individual streams analogously to Example 1

| Stream (1) (fl.) | | Stream (2) | | Stream (3) (g.) | |
|---|---|---|---|---|---|
| MeOH | 2009 g/h | MeOH (fl) | | 502 g/h O$_2$ | 172 g/h |
| Stream 4 (g.) | | Stream 5 (fl.) | | Stream 6 (g.) | |
| NO | 1266 g/h | MeOH | | 74 g/h CO$_2$ | 3365 g/h |
| NO$_2$ | 1000 g/h | HNO$_3$ | | 40 g/h NO | 12 g/h |
| CO$_2$ | 3365 g/h | Water | | 560 g/h MeOH | 421 g/h |
| | | | | MeONO | 3840 g/h |
| | | | | Water | <1.5 g/h |
| | | | | HNO$_3$ | 0 g/h |

The product gas mixture (stream (6)) had a temperature of 35° C. on leaving the heat exchanger III.

Example 3

Preparation of Methyl Nitrite by Reaction, After Separating Off the Condensable Reaction Products, of the Returned Cycle Gas Stream of a Typical Methyl-Nitrite-Consuming and Nitrogen-Monoxide-Producing Process With Oxygen and Methanol Performance of the trial and designation of the individual streams analogously to Example 1

| Stream (1) (fl.) | | Stream (2) | | Stream (3) (g.) | |
|---|---|---|---|---|---|
| MeOH | 1730 g/h | MeOH (fl) | | 401 g/h O$_2$ | 496 g/h |
| Stream 4 (g.) | | Stream 5 (fl.) | | Stream 6 (g.) | |
| NO | 1845 g/h | MeOH | | 84 g/h CO$_2$ | 4043 g/h |
| MeOH | 362 g/h | HNO$_3$ | | 39 g/h NO | 23 g/h |
| CO$_2$ | 4043 g/h | Water | | 535 g/h MeOH | 480 g/h |
| MeONO | 190 g/h | | | MeONO | 3861 g/h |
| | | | | Water | <2.0 g/h |
| | | | | HNO$_3$ | 0 g/h |

The product gas mixture (stream (6)) had a temperature of 35° C. on leaving the heat exchanger III.

What is claimed is:

1. A process for the preparation of a C$_1$–C$_4$-alkyl nitrite by reaction of a C$_1$–C$_4$-alkanol with nitrogen oxide and oxygen, in a reactor designed as a scrubber column, at 10° to 150° C. and 0.5 to 6 bar, and at a reaction time of 1 to 500 seconds, wherein the nitrogen oxide and oxygen is fed into the lower part of the reactor, said nitrogen oxide being nitrogen monoxide either alone or in combination with a member selected from the group consisting of $N_2O_3$, $NO_2$, $N_2O_4$ and mixtures thereof, wherein the NO fed is in an amount that is more than 50% of the nitrogen oxide, based on the total gram atoms of Nitrogen in said nitrogen oxide, and wherein said nitrogen oxide is undiluted or diluted with one or more inert gases, the proportion of said inert gas or gases being 0–90% by volume of all gases used, the amount of oxygen being 0.15–0.3 moles per mole of NO which exceeds the number of moles of $NO_2$, each mole of dinitrogen tetroxide being counted as two moles of nitrogen dioxide for the purpose of calculating said amounts, and wherein the total amount of $C_1$–$C_4$-alkanol used is 0.8 to 2 moles per gram atom of nitrogen in the nitrogen oxide, part of which is used in the lower part of the reactor and part of which is used at the reactor head, wherein said alkanol used at the lower part of the reactor is atomized using an inert gas, the oxygen or both, and is in an amount of 5 to 60% of the total amount of alkanol used, while the remainder of said alkanol is used at the reactor head.

2. The process of claim 1, wherein NO is present in an amount of 51–100% of the total amount of gram atoms of Nitrogen of the nitrogen oxides.

3. The process of claim 2, wherein said amount of NO is 70–100%.

4. The process of claim 3, wherein said NO is 80–100%.

5. The process of claim 1, wherein the nitrogen oxide is diluted with an inert gas selected from the group consisting of $CO_2$, $N_2$, Ar, He and mixing thereof wherein the inert gas is 10 to 80% by volume of all gases used.

6. The process of claim 5, wherein the inert gas is $CO_2$, $N_2$ or a mixture thereof.

7. The process of claim 5 wherein the inert gas is 20 to 70% by volume of all gases used.

8. The process of claim 1, wherein the amount of $C_1$–$C_4$-alkanol used is 1–1.5 moles per gram atom of nitrogen of the nitrogen oxides and 10–50% of said amount is fed into the lower part of the reactor.

9. The process of claim 8, wherein 1 to 1.2 moles of $C_1$–$C_4$-alkanol is used per gram atom of nitrogen of the nitrogen oxide.

10. The process of claim 8, wherein the alkanol fed into the lower part of the reactor is an amount of 10 to 30% of the total amount of alkanol used.

11. The process of claim 1, wherein the amount of oxygen used is 0.2–0.27 moles per mole of NO which exceeds the number of moles of $NO_2$.

12. The process of claim 11, wherein the amount of oxygen used is 0.23–0.25 moles per mole of NO which exceeds the number of moles of $NO_2$.

13. The process of claim 1, wherein the $C_1$–$C_4$-alkanol proportion used in the lower part of the reactor further comprises the nitrogen oxides, the oxygen and optionally either an inert gas or inert gas mixture.

14. The process of claim 1, wherein said alkanol is a $C_1$–$C_2$-alkanol and said alkyl nitrite is a $C_1$–$C_2$-alkyl nitrite.

15. The process of claim 14, wherein said alkanol is methanol and said alkyl nitrite is methyl nitrite.

16. The process of claim 1, wherein a pressure of 0.8 to 5 bar is employed.

17. The process of claim 1, wherein a temperature of 30°–100° C.

18. A process of claim 1, wherein a residence time of 5 to 300 seconds is set.

19. The process of claim 1, wherein said nitrogen oxide originates in whole or in part from a chemical process in which $C_1$–$C_4$-alkyl nitrite is used and nitrogen oxides are formed as by-products.

* * * * *